United States Patent [19]

Raabe et al.

[11] 4,088,764
[45] May 9, 1978

[54] PHARMACEUTICALLY ACTIVE DERIVATIVES OF 1-PHENOXY-3-AMINO-PROPAN-2-OL

[75] Inventors: Thomas Raabe, Rodenbach; Otto Grawinger, Frankfurt am Main; Josef Scholtholt, Mittelbuchen; Rolf-Eberhard Nitz, Bergen-Enkheim; Eckhard Schraven, Frankfurt am Main, all of Germany

[73] Assignee: Cassella Farbwerke Mainkur Aktiengesellschaft, Germany

[21] Appl. No.: 531,344

[22] Filed: Dec. 10, 1974

[30] Foreign Application Priority Data

Dec. 27, 1973  Luxembourg .......................... 34590

[51] Int. Cl.² ................... A61K 31/505; C07D 239/26
[52] U.S. Cl. .................................. 424/251; 542/416; 544/293.86; 260/326.5; 544/58; 424/246; 424/248; 544/131; 424/250; 424/267; 544/114; 424/270; 424/273; 544/120; 424/274; 424/275; 544/122; 424/285; 544/139; 544/140; 544/141; 544/133; 544/146; 544/152; 544/224; 544/238; 544/335; 544/336; 544/406; 260/307 FA; 260/293.86; 260/326.35; 260/326.25; 260/306.8 R; 260/326.36; 260/332.2 R; 260/332.3 R; 260/347.3; 260/347.5; 548/378; 548/374; 548/336; 548/343; 548/342

[58] Field of Search ................... 260/256.4 R, 240 R; 424/251

[56] References Cited

U.S. PATENT DOCUMENTS

| | | |
|---|---|---|
| 3,646,057 | 2/1972 | Beaman et al. ................ 260/256.4 R |
| 3,686,206 | 8/1972 | Posselt et al. ................ 260/256.4 R |
| 3,830,806 | 8/1974 | Raabe et al. ................ 260/296 AE |
| 3,852,291 | 12/1974 | Augstein et al. ............. 260/256.4 R |
| 3,940,406 | 2/1976 | Raabe et al. ................ 260/296 AE |
| 3,969,363 | 7/1976 | Raabe et al. ................ 260/296 AE |

Primary Examiner—Donald G. Daus
Assistant Examiner—James H. Turnipseed
Attorney, Agent, or Firm—Berman, Aisenberg & Platt

[57] ABSTRACT

The present invention relates to new pharmacologically valuable derivatives of 1-phenoxy-3-amino-propan-2-ol having the formula

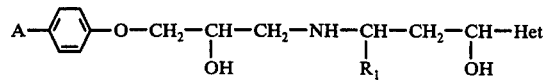

Wherein A denotes $-CH_2$-alkoxy, -O-alkoxyalkyl, -O-hydroxyalkyl, or

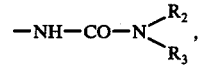

$R_1$ denotes hydrogen or methyl, Het denotes the radical of a pyrrole, pyrazole, imidazole, furane, thiophene, thiazole, pyridine, pyridazine, pyrimidine or pyrazine, which can additionally be substituted by one or more methyl groups, said radical is linked through a C atom, and $R_2$ and $R_3$ denote hydrogen, alkyl, alkenyl or cycloalkyl or conjointly with the N atom to which they are linked, and optionally with a further oxygen or sulfur hetero-atom, denote a saturated, 5-membered or 6-membered, monocyclic, heterocyclic structure, and alkyl radicals contain 1 to 4 carbon atoms, alkoxy radicals contain 1 to 4 carbon atoms, alkenyl radicals contain 3 or 4 carbon atoms and cycloalkyl radicals contain 5 to 7 carbon atoms; and aldehyde condensation products and acid addition salts thereof.

13 Claims, No Drawings

PHARMACEUTICALLY ACTIVE DERIVATIVES OF 1-PHENOXY-3-AMINO-PROPAN-2-OL

The invention relates to new, pharmacologically valuable derivatives of 1-phenoxy-3-aminopropan-2-ol of the general formula I

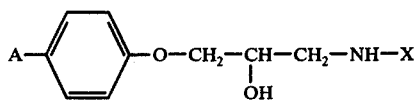

wherein X denotes

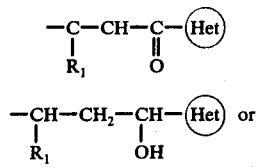

A denotes —CH$_2$-alkoxy, —O-alkoxyalkyl, —O-hydroxyalkyl or

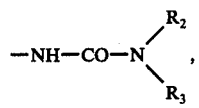

R$_1$ denotes hydrogen or methyl, (Het) denotes an aromatic or quasi-aromatic, 5-membered or 6-membered, monocyclic ring which is linked through a C atom which has one or 2 nitrogen, oxygen and/or sulphur hetero-atoms and which can be substituted additionally by one or more methyl groups, and R$_2$ and R$_3$ denote hydrogen, alkyl, alkenyl or cycloalkyl or, conjointly with the N atom to which they are linked, and optionally with a further oxygen or sulphur hetero-atom, denote a saturated, 5-membered or 6-membered, monocyclic, heterocyclic structure, and alkyl radicals contain 1 to 4 carbon atoms, alkoxy radicals contain 1 to 4 carbon atoms, alkenyl radicals contain 3 or 4 carbon atoms and cycloalkyl radicals contain 5 to 7 carbon atoms.

The invention also emcompasses the acid addition salts and aldehyde condensation products of the compounds according to the invention, of the general formula I.

Products according to the invention which are preferred are those in which X has the meaning of

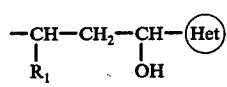

By the compounds of the general formula I, there are also understood, within the scope of the present invention, possible stereoisomers and optically active compounds and mixtures thereof, particularly the racemate.

Preferred substituents under the definition (Het) are radicals of pyrrole, pyrazole, imidazole, furane, thiophene, thiazole, pyridine, pyridazine, pyrimidine and parazine. These radicals can be additionally substituted with one or more methyl groups, preferably one, two or three methyl groups.

If the substituents R$_2$ and R$_3$, conjointly with the nitrogen atom to which they are linked, and optionally with an additional oxygen or sulphur hetero-atom, form a saturated, 5-membered or 6-membered, monocyclic, heterocyclic structure, they are to be understood particularly as the radicals of pyrrolidine, piperidine, morpholine and thiomorpholine.

The aldehyde condensation products of compounds of the general formula I are oxazolidines of the formula II

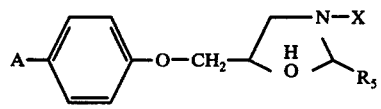

which are formed in the condensation of compounds of the general formula I with an aldehyde of the formula

R$_4$ — CHO in which R$_4$ represents hydrogen or a lower alkyl radical having up to 4 C atoms.

Inorganic and organic acids are suitable for the formation of salts with the compounds of the general formula I. Examples of suitable acids are hydrogen chloride, hydrogen bromide, phosphoric acid, sulphuric acid, oxalic acid, lactic acid, tartaric acid, acetic acid, salicylic acid, benzoic acid, citric acid, adipic acid or naphthalene-1,5-disulphonic acid. Pharmaceutically acceptable acid addition salts are preferred.

In order to prepare the compounds of the general formula I, a 1-phenoxy-3e-aminopropane-aminopropan-2-ol of the general formula III is reacted with a compound of the general formula IV with elimination of H-Y to form a compound I according to the invention:

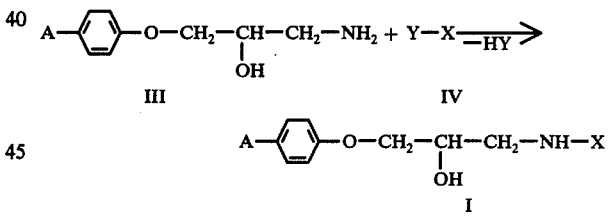

In this, X has the meaning already mentioned and Y denotes halogen, particularly chlorine or bromine, and, if X represents

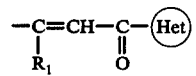

also —OH, —OK or —ONa.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, for example acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. The solvents used are, in particular, polar solvents, such as, for example, alcohols. Examples of suitable alcohols are methanol, ethanol, isopropanol, tert.-butanol and the like. The reaction is carried out at temperatures from 20° C up to the reflux temperature of the solvent or dispersing agent used. The reaction frequently takes place even at normal temperature.

If X represents 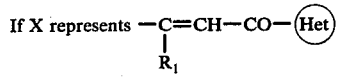

the reaction is accelerated by adding an acid, preferably hydrogen chloride. Examples of other suitable acids are carboxylic acids, such as, for example, formic acid, acetic acid, propionic acid and butyric acid; sulphonic acids, such as, for example, benzenesulphonic acid and p-toluenesulphonic acid; and mineral acids, such as, for example, sulphuric acid and phosphoric acid. If a compound of the general formula IV having Y = OH is employed, even catalytic amounts of the acid, for example of acetic acid or formic acid, are adequate to accelerate the reaction. If compounds of the general formula IV having Y = ONa or OK are employed, about 1 mol of the acid is added. Instead of adding an acid, it is also possible to accelerate the reaction by employing the compound of the general formula III in the form of a salt, for example the hydrohalide. If a compound of the general formula IV in which Y represents halogen is employed, it is also possible to employ this compound of the general formula IV in the form of the hydrohalide. In the preparative process according to the invention, the acid addition salts of the compound I can be formed, or, on adding an acid-binding agent such as potassium carbonate or sodium carbonate, the free amines can be formed.

Depending on the meaning of X, the starting compounds of the general formula IV which are required are either derivatives of the propen-1-one of the general formula V or of the propan -1ol of the general formula VI:

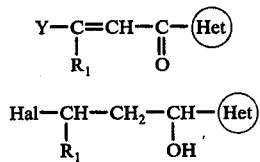

In these, Y has the meaning already indicated and Hal represents halogen, particularly chlorine or bromine. Starting compounds of the general formula V in which $R_1$ denotes methyl, and which therefore have the general formula V$a$

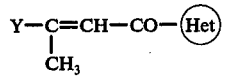

can be obtained either by recting an ester of a heterocyclic carboxylic acid of the general formula VII$a$, particularly a methyl or ethyl ester, with acetone under the conditions of an alkaline ester condensation, or by reacting an acetic acid ester, particularly methyl or ethyl acetate, under analogous conditions with a methyl ketone of the general formula VII$b$. This gives the sodium salt or potassium salt of the formula VII or VIII, respectively:

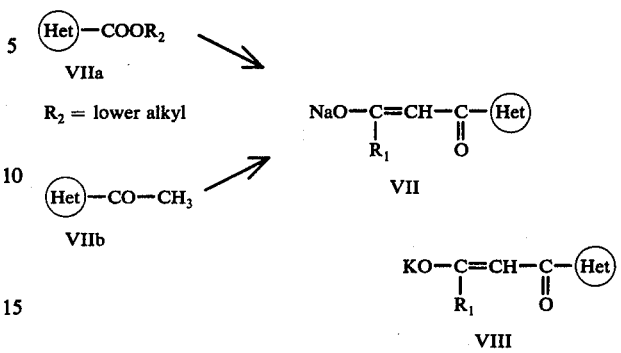

Starting compounds of the general formula V in which $R_1$ denotes hydrogen, and which therefore have the general formula V$b$

   V$b$ can be obtained by reacting methyl ketone of the general formula VII$b$, under the conditions of an alkaline ester condensation, with a formic acid ester, particularly methyl formate or ethyl formate.

This give the sodium salt or potassium salt of the formula VII or VIII respectively, in which $R_1$ denotes hydrogen.

The free vinyl alcohols of the formula IX, which are tautomeric with the corresponding ketone derivates of the formula X:

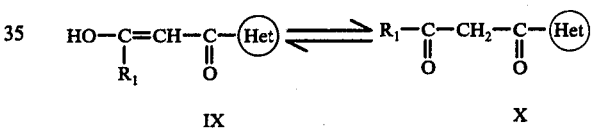

are obtained from these salts by hydrolysis.

By reacting the compounds of the formula IX or X with suitable halogenating agents, such as, for example, thionyl chloride or phosphorus tribromide, the corresponding 3-halogeno-prop-2-en-1-ones of the general formula XI

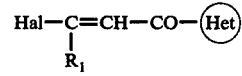

wherein Hal represents halogen, particularly chlorine or bromine, are obtained. Compounds of the general formula VI can be prepared from the corresponding compounds of the formula XI by hydrogenation, appropriately by means of complex hydrides, such as, for example, lithium aluminium hydride, sodium borohydride or the like.

The compounds of the general formula III which are required as starting compounds can be prepared by reacting, with ammonia or with compounds which split off ammonia, a compound of the general formula XII or XIII,

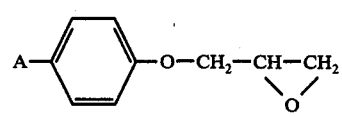   XII

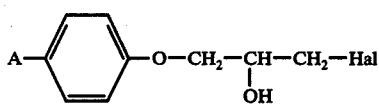

XIII

Hal in XIII denoting a halogen atom, particulary chlorine or bromine, or a mixture of a compound XII with a compound XIII which is identically substituted in the phenyl nucleus. The reaction can be carried out under atmospheric pressure or under elevated pressure at ambient temperature and can be accelerated or brought to completion by supplying heat, for example by heating to 70° C.

The compounds of the general formulae XII and XIII can be prepared by reacting a phenol of the general formula XIV

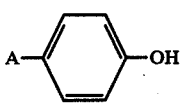

XIV with an epinhalogenohydrin, appropriately with epichlorohydrin or epibromohydrin. A compound of the general formula XII or XIII or a mixture of compounds of the general formulae XII and XIII is formed in the course thereof, depending on the reaction conditions. The reaction product formed can be isolated before being further reacted with ammonia, but it can also be directly reacted further without isolation.

Compounds of the general formula I can be prepared by reacting a compound of the general formula XV with a compound of the general formula XVI:

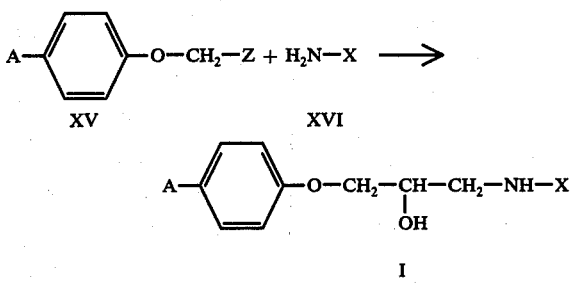

In this, X has the meaning already mentioned and Z denotes:

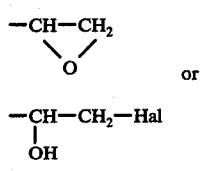

wherein Hal represents a halogen atom, particularly chlorine or bromine.

The reaction is normally carried out in a suitable solvent of dispersing agent in which the reactants are dissolved or suspended. Examples of solvents or dispersing agents of this kind are aromatic hydrocarbons, such as, for example, benzene, toluene or xylene; ketones, for example acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. The solvents used are, in particular, polar solvents, such as, for example, alcohols. Examples of suitable alcohols are methanol, ethanol, isopropanol, tert.-butanol and the like. The reaction is carried out at temperatures from 20° C up the reflux temperature of the solvent or dispersing agent used. The reaction frequently takes place at temperatures of 40 and 50° C.

It can be advisable to employ the starting compound of the general formula XVI in a one- to 10-fold molar excess and/or to add the reaction component of the general formula XV in a dissolved or suspended form to the dissolved or suspended reaction component of the general formula XVI. The molar ratio between the compounds of the general formulae XV and XVI can be 1 : 1 to 1 : 10 and optionally even more.

In carrying out the reaction, a compound of the general formula XII or of the general formula XIII or a mixture of both these compounds, can be employed as the compound of the general formula XV.

If a compound of the general formula XIII is present, it is also possible to carry out the reaction in the presence of acid-binding agents, such as potassium carbonate, sodium carbonate and the like. Without an acid-binding agent, the hydrohalides of the compounds of the general formula I are then usually obtained.

The preparation of the starting compounds of the general formula XVI is described in the Examples.

In order to prepare the compounds of the general formula I it is also possible to react a phenol of the general formula XIV with a compound of the general formula XVII to give a compound of the general formula I:

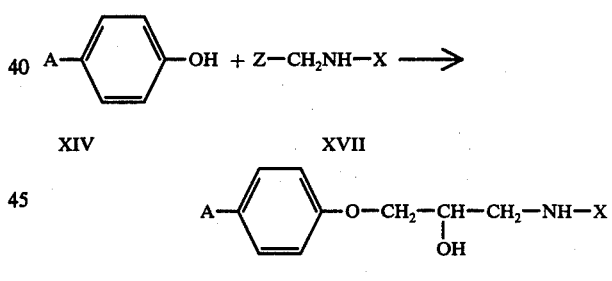

In this, X has the meaning already mentioned and Z denotes:

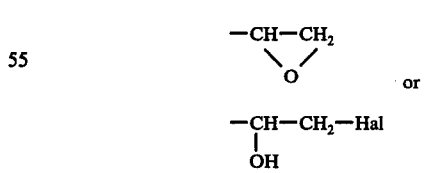

wherein Hal represents a halogen atom, particularly chlorine or bromine.

This reaction too is normally carried out in a suitable solvent or dispersing agent in which the reactants are dissolved or suspended. Examples of solvents or dispersing agents of this kind are aromatic hydrocarbons, such as, for example, benzene, toluene or xylene, ketones, such as, for example, actone or methyl ethyl ketone; halogenated hydrocarbons, such as, for example, chloroform, carbon tetrachloide, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. Polar solvents, in particular, such as, for example, alcohols, are used as the solvent. Examples of suitable alcohols are methanol, ethanol, isopropanol, tert.-butanol and the like. If Z deonotes

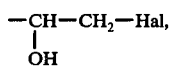

the reaction is generally carried out in the presence of an acid-binding agent, such as, for example, potassium carbonate, sodium carbonate or sodium bicarbonate. The reaction can also be carried out in aqueous alkalis, such as, for example, dilute sodium hydroxide or potassium hydroxide solution. The reaction temperature can be from 20° up to the reflux temperature of the solvent or dispersing agent used.

It can be advisable to employ the starting compound of the general formula XVII in a one- to 10-fold molar excess and/or to add the reaction component of the general formula XIV in a dissolved or suspended form to the dissolved or suspended reaction component of the general formula XVII. The molar ratio between the compounds of the general formula XIV and XVII can be 1 : 1 to 1 : 10 and optionally even more.

In carrying out the reaction it is possible to employ a compound of the general formula XVIII or of the general formula XIX or a mixture of both these compounds, as the compound of the general formula XVII.

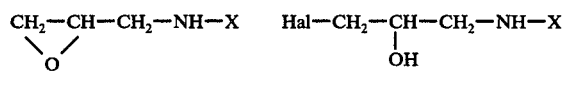

XVIII          XIX

The compounds of the general formula XVIII and XIX can be prepared by reacting compounds of the general formula XVI with an epihalogenohydrin, appropriately with epichlorohydrin or epibromohydrin. Compounds of the general formula XVIII or XIX or a mixture of compounds of the general formula XVIII and XIX are formed in the course thereof, depending on the reaction conditions. The reaction product formed can be isolated in order to be reacted further, but it can also be directly reacted further without isolation.

The compounds of the general formula I in which X denotes the radical

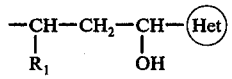

and which therefore have the general formula XX

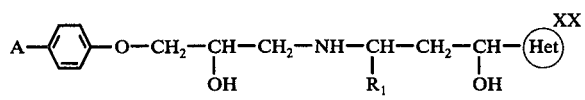

can also be prepared by hydrogenating a compound of the general formula XXI, XXII or XXIII

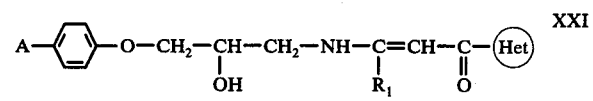

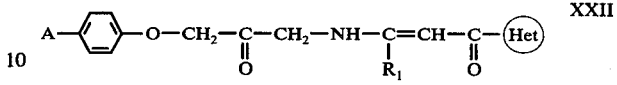

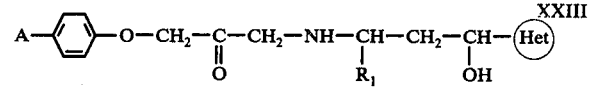

The compounds of the general formula I in which X denotes the radical

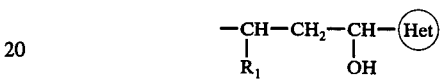

and $R_1$ represents hydrogen, and which therefore have the general formula

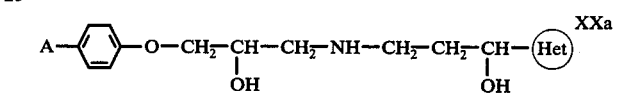

can, in addition, also be prepared by hydrogenating compounds of the general formula XXIIIa or XXIIIb

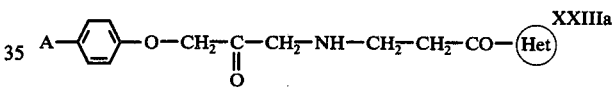

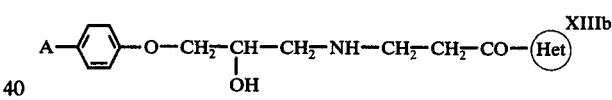

It is advantageous to employ, for the hydrogenation, complex hydrides, such as, for example lithium aluminum hydride, sodium borohydride and the like. The reaction is carried out under the reaction conditions which are known for these hydrides, normally in alcohol or an alcohol/water mixture at room temperature or elevated temperature, for example while boiling under reflux. In some cases the hydrogenation can also be carried out catalytically, for example using a palladium-charcoal catalyst.

The starting compounds of the general formula XXI are compounds according to the invention, of the general formula I, wherein X represents the radical

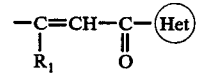

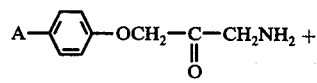

XXIV

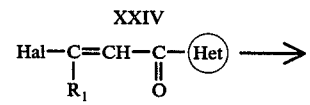

XI

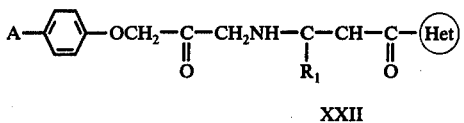

XXII

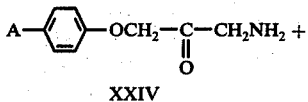

XXIV

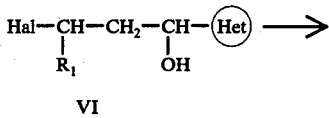

VI

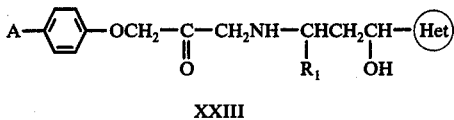

XXIII

The reaction between the compounds of the general formula XXIV and XI or XXIV and VI, respectively, is carried out in solvents such as benzene, toluene, chloroform, methylene chloride, dioxane and the like, at normal temperature or elevated temperature in the presence of at least molar quantities of acid-binding agents, such as potassium carbonate or sodium carbonate, or in the absence of acidbinding agents, the hydrohalides of the compounds XXII or XXIII being usually obtained in the latter case.

Compounds of the general formula XXIV can be prepared, for example, by gentle oxidation of compounds of the general formula III

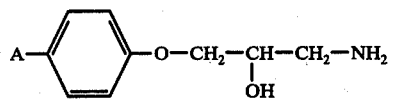

III

Starting compounds of the general formula XXIIIa can be prepared by a Mannich reaction from a compound of the general formula XXIV, formaldehyde and a methyl ketone of the general formula VIIb.

Compounds of the general formula XXIIIb can be prepared by a Mannich reaction from a compound of the general formula III, formaldehyde and a methyl ketone of the general formula VII*b*.

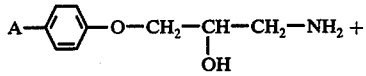

III

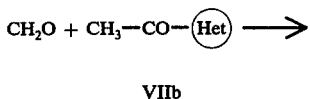

VIIb

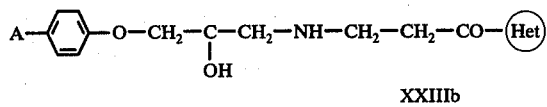

XXIIIb

Aldehyde condensation products of the formula II are obtained by reacting, in a diluent or solvent, for example ethanol, preferably in the presence of an acid catalyst, for example acetic acid or hydrochloric acid, and preferably at elevated temperature, compounds of the general formula I with an aldehyde of the formula $R_3$—CHO wherein $R_3$ denotes hydrogen or a lower alkyl radical. The water formed in the reaction can be removed by azeotropic distillation with the aid of an entraining agent, for example benzene, or by means of a dehydrating agent, such as anhydrous potassium carbonate.

The acid addition salts of the compounds of the general formula I can be prepared from the components in a manner which is in itself known. The use of a diluent is generally advantageous here, the di-salts of the compounds of the general formula I being generally obtained when there is an excess of acid. The mono-acid addition salts are obtained either by controlled addition of only 1 mol of acid or by partial hydrolysis of the di-acid addition salts.

The compounds of the general formula I, their aldehyde condensation products II and their pharmaceutically acceptable acid addition salts possess valuable pharmaceutical properties. Thus they are suitable, for example, for the treatment or prophylaxis of heart diseases. In addition, some of them have very marked β-adrenolytic (β-adrenergic blocking) or anti-arrhythmic properties. The compounds can, therefore, be used as pharmaceutical preparations, on their own, in mixtures with one another or mixed with diluents or excipients which are pharmaceutically unobjectionable. The pharmaceutical preparations can be present in the form of, for example, tablets, capsules, aqueous or oily solutions or suspensions, emulsions, injectable aqueous or oily solutions or suspensions, dispersible powders or aerosol mixtures. Besides the compounds of the general formula I, the pharmaceutical preparations can also contain one or more other pharmaceutically active substances, for example sedatives, such as, for example, Luminal, Meprobamat and Chlorpromazine; vasodilators, such as, for example, glycerol trinitrate and carbochromene; diuretics, such as, for example, chlorothiazide; agents for tonicising the heart, such as, for example, digitalis preparations; hypotension agents, such as, for example, Rauwolfia alkaloids; and broncho-dilators and sympathomimetic agents, such as, for example, Isoprenalin and Ephedrin.

Compounds according to the invention, of the general formula I, which are particularly preferred are those in which X has the meaning:

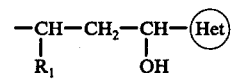

The blocking action of the compounds according to the invention on the β1-receptors of the heart and on the β2-receptors of the cardiovascular system was investigated as follows: the blood pressure in the left-hand ventricle was measured on mongrel dogs of both sexes under an anaesthesia by Chloralose-urethane-morphine and the pressure signal was continuously differentiated by means of an analogue computer (BRUSH Instruments, Cleveland/Ohio) and, inter alia, the rate of pressure increase (Dp/dt) was recorded. In addition, the perfusion of a femoral artery was measured by means of an electromagnetic flowmeter (Model M4000 of Messrs. Statham) and the perfusion was recorded in ml/minute.

Alterations in the maximum rate of pressure increase (Dp/dt max.) compared with the zero value were induced by intravenous administration of Isoproterenol (0.5 gamma/kg), a known sympathomimetic agent ($\beta$1-reaction), while alterations of the peripheral perfusion, compared with the zero value, were induced by intraarterial administration of Isoproterenol (0.05 gamma/kg) ($\beta$2-reaction) (D. DUNLOP and R.G. Shanks: Selective blockade of adrenoceptive beta-receptors in the heart. Brit. J. Pharmac. Chemother. (1968) 32, 201–218).

The substances to be tested for $\beta$-receptor blocking were administered intravenously in increasing dosages to the animals which had been anaesthetised and stimulated by means of Isoproterenol, and the quantity of substance was determined at which a 50 % inhibition of the two reactions caused by Isoproterenol occurred (ED50). The ED50 values of the $\beta$1-receptor inhibition (mg/kg intravenous) and the ED50 values of the $\beta$2-receptor inhibition (mg/kg intravenous) are given in the table which follows. In addition, the relative ED 50 values were calculated for both cases, taking as a basis 4-(2-hydroxy-3-isopropylaminopropoxy)-acetanilide, which was employed as a reference substance, the ED 50 values of the latter being made equivalent to 100. The quotient derived from the ED 50 of the $\beta$2-receptor inhibition and the ED 50 of the $\beta$1-receptor inhibition represents a measure of the cardioselective action of the substances under investigation. The higher this quotient is, the better the cardioselective action. If the quotient of the reference substance 4-(2-hydroxy-3-isopropylamino-propoxy)-acetanilide is made equivalent to 1, the relative factor indicates how much better the cardioselective action of the compound according to the invention is than the reference substance.

Furthermore, the relative ED 50 values of the $\beta$1-receptor inhibition (column 2 of the table which follows) are a measure of the effectiveness of the substances to be tested. The lower the figures are, the more active the substances, that is to say the smaller the quantity required for the production of the therapeutic effect.

4-(2-Hydroxy-3-isopropylamino-propoxy)-acetanilide, which is employed as the reference substance, is a preparation which is commercially available as $\beta$-blocker and which carries the international unprotected trade name "Practolol".

| Substance under investigation | $\beta$1-receptor inhibition ED 50 (mg/kg intravenous) | Relative $\beta$-1-receptor inhibition (reference substance = 100) | $\beta$2-receptor inhibition ED 50 (mg/kg intravenous) | Relative $\beta$-2-receptor inhibition (reference substance = 100) | Quotient: ED 50 $\beta$2-receptor inhibition / ED 50 $\beta$1-receptor inhibition | Quotient, on basis of reference substance = 1 |
|---|---|---|---|---|---|---|
| 1-(p-[2-Hydroxy-ethoxy]-phenoxy)-3-(1-[2-methyl-pyridyl-5]-1-hydroxy-butyl(3)-amino)-propan-2-ol | 0.073 | 30.7 | 8.14 | 30.7 | 112 | 1 |
| 1-(p-Methoxybutoxy-phenoxy)-3-(1-[2,4-dimethyl-pyrimidyl-5]-1-hydroxy-butyl(3)-amino)-propan-2-ol | 0.089 | 37.4 | 15.59 | 58.8 | 176 | 1.6 |
| 1-(p-Ethylureido-phenoxy)-3-(1-[2,4-dimethyl-pyrimidyl-5]-1-hydroxy-butyl(3)-amino)-propan-2-ol | 0.093 | 39.1 | 12.79 | 48.3 | 137 | 1.2 |
| 1-(p-Allylureido-phenoxy)-3-(1-[2,4-dimethyl-pyrimidyl-5]-1-hydroxy-butyl(3)-amino)-propan-2-ol | 0.019 | 7.9 | — | | — | |
| 1-(p-Isopropylureido-phenoxy)-3-(1-[2,4-dimethyl-pyrimidyl-5]-1-hydroxy-butyl(3)-amino)-propan-2-ol | 0.022 | 9.2 | 2.71 | 10.2 | 124 | 1.1 |
| 1-(p-Cyclohexylureido-phenoxy)-3-(1-[pyridyl-3]-1-hydroxy-butyl(3)-amino)-propan-2-ol | 0.003 | 1.3 | 1.02 | 3.8 | 409 | 2.9 |
| 1-(p-Cyclohexylureido-phenoxy)-3-(1-[2,4-dimethyl-pyrimidyl-5]-1-hydroxy-butyl(3)-amino)-propan-2-ol (as L-(+)-tartrate) | 0.011 | 4.6 | 1.38 | 5.2 | 128 | 1.1 |
| 1-(p-Cyclohexylureido-phenoxy)-3-(1-[2-methyl-pyridyl-5]-1-hydroxy butyl(3)-amino)-propan-2-ol | 0.006 | 2.5 | 1.57 | 5.9 | 245 | 2.4 |
| 1-(p-Ethoxymethylene-phenoxy)-3-(1-[2,4-dimethyl-pyrimidyl-5]-1-hydroxy-butyl(3)-amino)-propan-2-ol (as L-(+)-tartrate) | 0.019 | 7.9 | 2.88 | 10.7 | 144 | 1.4 |
| 1-(p-Ethoxymethylene-phenoxy)-3-(1-[pyridyl-3]-1-hydroxy-butyl(3)-amino)-propan-2-ol | 0.010 | 4.2 | — | | — | |
| 1-(p-Ethylureido-phenoxy)-3-(1-[pyridyl-3]-1-hydroxy-butyl(3)-amino)-propan-2-ol | 0.013 | 5.5 | — | | — | |
| 1-(p-Ethoxyethoxy-phenoxy)-3-(1-[pyridyl-3]-1-hydroxy-butyl(3)-amino)-propan-2-ol | 0.009 | 3.8 | 2.76 | 10.1 | 296 | 2.7 |
| Reference substance: 4-(2-Hydroxy-3-isopropyl- | | | | | | |

| Substance under investigation | β1-receptor inhibition ED 50 (mg/kg intravenous) | Relative β-1-receptor inhibition (reference substance = 100) | β2-receptor inhibitin ED 50 (mg/kg intravenous) | Relative β-2-receptor inhibition (reference substance = 100) | Quotient: ED 50 β2-receptor inhibition / ED 50 β1-receptor inhibition | Quotient, on basis of reference substance = 1 |
|---|---|---|---|---|---|---|
| amino-propoxy) acetanilide | 0.238 | 100 | 26.505 | 100 | 110 | 1 |

A tablet containing a compound according to the invention and having a total weight of 100 mg, can have the following composition, for example:

5 mg of 1-(p-allylureidophenoxy)-3-(1-[2,4-dimethylpyrimidyl-5]-1-hydroxybutyl(3)-amino)-propan-2-ol
10 mg of colloidal silicic acid (Aerosil)
72.5 mg. of DAB7 lactose
1.5 mg of gelatine
8.5 mg of DAB7 maize starch and
2.5 mg of Mg stearate USPXVIII Depending on the severity of the case to be treated, it is possible, for example, to administer 1 to 2 of these tablets to a patient three times daily.

The preparation of the compounds of the general formula I is illustrated in greater detail in the following examples. The compounds are frequently oils which cannot be distilled, so that in some cases no melting point is shown. However, in all cases the structure indicated has been checked by molecular analysis and/or the infrared spectrum or nuclear resonance spectrum.

EXAMPLE 1

5.1 g of 1-(p-methoxybutoxyphenoxy)-3-aminopropan-2-ol

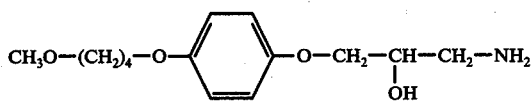

are dissolved in 50 ml of ethanol, 3.3 g of nicotinoylacetone

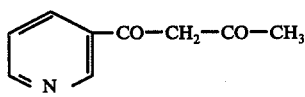

are then added and, after adding 1 drop of formic acid, the solution is heated under reflux for 3 hours. The solution is then concentrated in vacuo. A solid residue remains, which is recrystallised from toluene.

This gives 1-(2-nicotinoyl-1-methylvinylamino-3-(p-methoxybutoxyphenoxy)-propan-2-ol of the formula

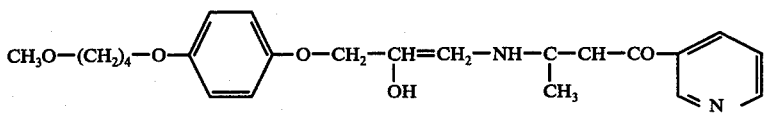

Melting point: 108° C
Analysis: ($C_{23}H_{30}N_2O_5$)
calculated: C 66.7 H 7.2 N 6.8;
found: 66.6 7.2 7.0,
Yield: 78% of theory.

The nicotinoyl-acetone required can be prepared either from nicotinic acid ethyl ester and anhydrous acetone in the presence of sodium ethylate in a known manner, for example following A. Ferenczy, Monatshefte fur Chemie page 674 (1897), or from acetylpyridine in accordance with the following instructions:

22.4 g of potassium tert.-butylate are suspended in 150 ml of anhydrous benzene, a mixture of 18.3 g of ethyl acetate and 24.2 g of 3-acetylpyridine is then added dropwise slowly, with stirring at 10° C, and the mixture is then allowed to stand at room temperature for 24 hours. The product is then filtered off and washed twice with anhydrous benzene, then twice with anhydrous ethanol and finally twice with diethyl ether. This gives the potassium salt of nicotinoyl-acetone in a yield of 77% of theory. The free nicotinoyl-acetone can be obtained practically quantitatively from the potassium salt by acid hydrolysis.

The 1-(p-methoxybutoxyphenoxy)-3-amino-propan-2-ol required can be prepared as follows:
4-(4-Methoxybutoxy)-phenyl benzyl ether

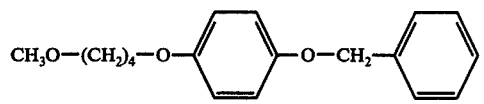

Melting point: 60-61°
is obtained in the usual manner (heating with acetone in the presence of excess potassium carbonate) from hydroquinone monobenzyl ether and (4-bromobutyl) methyl ether.

Hydrogenation of this in methanolic solution (Raney nickel, 50 atmospheres gauge of $H_2$, 50°) gives 4-(4-methoxybutoxy)-phenol.

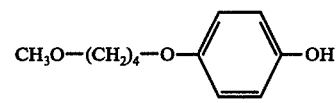

as an oil, boiling point 138–143°/0.1 mm Hg.

This phenol can be reacted with epichlorohydrin in the usual manner; the crude 4-(4-methoxybutoxy)-phenyl glycidyl ether

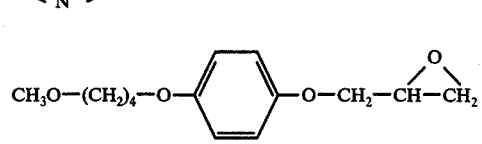

thus obtained is stirred, directly, with excess saturated aqueous-alcoholic ammonia solution for 20 hours at room temperature. The reaction mixture is evaporated under reduced pressure and the residue is distilled in vacuo; this gives, in a 57% yield, 1-(4-[4-methoxybutoxy]-phenoxy)-3-amino-propan-2-ol.

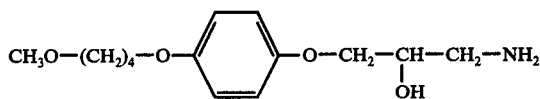

boiling point 207°–219°/0.1 mm Hg; melting point: 84°–88°. Melting point: 92°–93° after recrystallisation from toluene or reprecipitation from dilute hydrochloric acid.

If β-bromoethyl ethyl ether is used instead of (4-bromobutyl) methyl ether, 4-(2-ethoxyethoxy)-phenyl benzyl ether

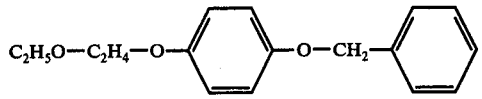

melting point: 35°–37° is obtained in an identical manner, and the following compounds are obtained from this in a corresponding manner, as indicated: 4-(2-ethoxyethoxy)-phenol

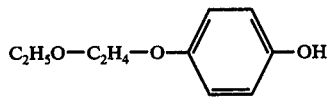

as an oil; 4-(2-ethoxyethoxy)-phenyl glycidyl ether

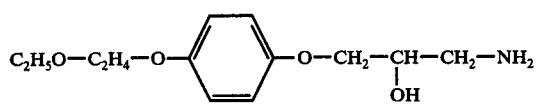

as a low-melting solid, boiling point 135°–143°/0.1 mm Hg, and 1-[4-(2-ethoxyethoxy)-phenoxy]-3-aminopropan-2-ol

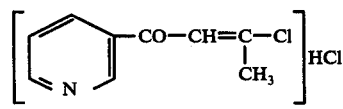

melting point: 84°–86°.

After condensation with nicotinoyl-acetone, as described initially, this gives 1-(2-nicotinoyl-1-methyl-vinylamino)-3-(p-ethoxyethoxy-phenoxy)propan-2-ol, melting point 88°–89°.

EXAMPLE 1a 6.1 g of 1-(p-cyclohexylureido-phenoxy)-3-amino-propan-2-ol of the formula

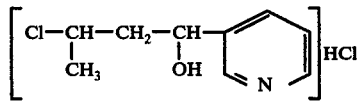

are dissolved in 50 ml of anhydrous toluene and 5.7 g of anhydrous potassium carbonate are added. A mixture of 4.4 g of 1-(β-pyridyl)-3-chloro-butan-1-ol hydrochloride of the formula $$\left[ Cl-CH-CH_2-CH \underset{CH_3}{\overset{}{|}} \underset{OH}{\overset{}{|}} \underset{N}{\bigcirc} \right] HCl$$

(prepared by reduction from 2-nicotinoyl-1-methyl-vinyl chloride hydrochloride described in Example 2) in 50 ml of anhydrous toluene is slowly added to the preceding mixture, whilst stirring and cooling, the whole is then heated for 18 hours whilst stirring, allowed to cool and filtered, the residue is dissolved in water and the solution is adjusted to pH 1 with 2 N hydrochloric acid. The acid solution is then washed three times with ethyl acetate, the pH is raised to 5, and the solution is again washed three times with ethyl acetate, then rendered alkaline to pH 9 with sodium carbonate solution and extracted three times with chloroform. The combined chloroform extracts are dried and concentrated in vacuo. 1-(p-Cyclohexylureido-phenoxy)-3-(1-hydroxy-1-pyridyl-(3)-butyl-3-amino)-propan-2-ol is thus obtained, as a colourles oil of the formula

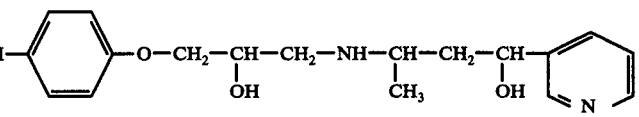

EXAMPLE 2

6.1 g of 1-(p-cyclohexylureido-phenoxy)-3-amino-propan-2-ol

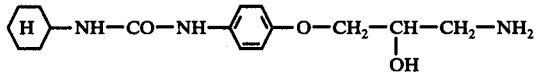

are dissolved in 50 ml of anhydrous toluene and 5.7 g of anhydrous potassium carbonate are added. A mixture of 4.4 g of 2-nicotinoyl-1-methylvinyl chloride hydrochloride of the formula $$\left[ \underset{N}{\bigcirc} -CO-CH=C-Cl \underset{CH_3}{\overset{}{|}} \right] HCl$$

(prepared from the sodium salt of nicotinoyl-acetone, which is first converted by means of HCl gas into the hydrochloride of free nicotinoyl-acetone and then, using thionyl chloride, into nicotinoyl-methylvinyl chloride hydrochloride) in 50 ml of anhydrous toluene is added slowly, with cooling and stirring, to this mixture and stirring is subsequently continued for 36 hours at room temperature. The product is then filtered and the residue is dissolved in water and the solution is rendered alkaline by means of sodium carbonate and extracted three times with chloroform. The chloroform extracts are concentrated, together with the original toluene filtrate, in vacuo at approx. 14 to 20 mm Hg. 1-(2-Nicotinoyl-1-methylvinylamino)-3-(p-cylcohexylureidophenoxy)-propan-2-ol is thus obtained after repeated recrystallisation from aqueous ethanol.

The same product is also obtained by reacting 1-(p-methoxybutoxyphenoxy)-2,3-epoxypropane

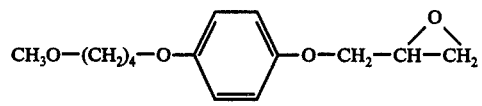

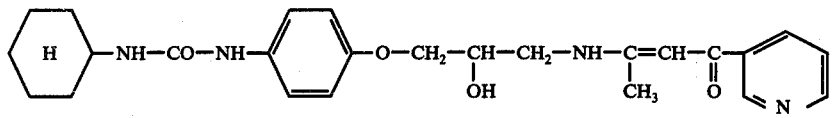

Melting point: 168° C
Analysis: ($C_{25}H_{32}N_4O_4$)
calculated: C 66.4 H 7.1 N 12.4;
found: 66.5 6.9 12.3;
Yield: 81% of theory.

(prepared by heating 4-methoxybutoxyphenol with epichlorohydrin and potassium carbonate in anhydrous toluene) with 1-(β-pyridyl)-3-aminobutan-1-ol

EXAMPLE 3

6.2 g of 1-(2-nicotinoyl-1-methylvinylamino)-3-(p-methoxybutoxyphenoxy)-propan-2-ol

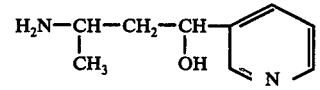

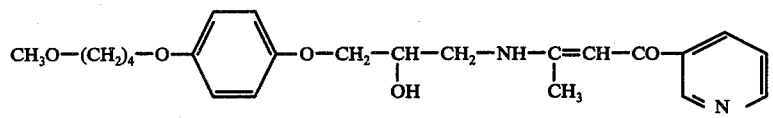

are dissolved in 65 ml of ethanol, the solution is heated under reflux and 2.8 g of sodium borohydride are added in portions at this temperature in the course of 40 minutes. The mixture is then allowed to boil under reflux for a further 11 hours. The solution is then concentrated in vacuo, the residue is dissolved in 40 ml of chloroform and 40 ml of water, the chloroform phase is separated off, the aqueous phase is extracted twice more with fresh chloroform and the combined chloroform phases are then concentrated in vacuo, after drying by means of sodium sulphate. An oil remains, which is dissolved in dilute aqueous hydrochloric acid. The hydrochloric acid solution is washed three times with ethyl acetate, then neutralised to pH 5 with aqueous sodium carbonate solution and again washed three times with ethyl acetate. The solution is then rendered alkaline, to pH 9, by means of sodium carbonate solution and extracted three times with chloroform. After washing with water and drying over sodium sulphate, the chloroform solution is concentrated in vacuo. The residual oil is then heated to 180° C in a vacuum of 0.1 mm Hg, a small amount of impurity being distilled off. The distillation residue is dissolved in absolute dioxane, treated with animal charcoal, filtered and concentrated in vacuo. This gives 1-(p-methoxybutoxyphenoxy)-3-(1-hydroxy-1-pyridyl-(3)-butyl-3-amino)-propan-2-ol as a colorless oil The 1-(β-pyridyl)-3-aminobutan-1-ol can be prepared as follows:

The potassium salt of nicotinoyl-acetone is first synthesised as indicated in Example 1. 2 g of the potassium salt of nicotinoyl-acetone are then suspended on 50 ml of ethanol and 1.6 g of benzylamine hydrochloride are added and the mixture is stirred at room temperature for 24 hours. The suspension is filtered and the residue is washed with ethanol. The filtrate, including the alcohol washings, is concentrated in vacuo. An oil remains, which becomes solid after a short time. The solidified oil, together with the residue left from the alcohol washings, is repeatedly triturated with water and is then recrystallised from ethanol. This gives N-(2-nicotinoyl-1-methylvinylamino)-benzylamine, melting point 102°–104°, in 88% yield.

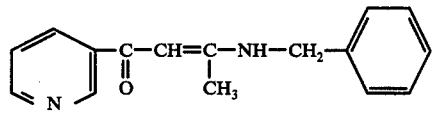

This gives, in a 62% yield, by reduction using sodium borohydride, analogously to the instructions for reduction in Example 3, 1-(β-pyridyl)-3-benzylaminobutan-1-

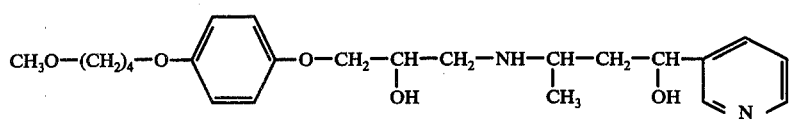

Analysis: ($C_{23}H_{34}N_2O_5$)
calculated: C 66.0 H 8.1 N 6.7
found: 65.8 8.2 6.5
Yield: 63% of theory.

ol (an oil)

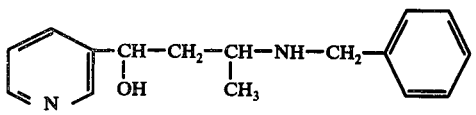

which can be debenzylated in the customary manner by means of hydrogen in an autoclave to give 1-(β-pyridyl)-3-aminobutan-1-ol (a viscous oil)

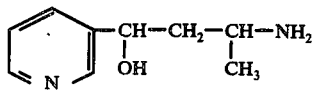

1-(β-Pyridyl)-3-aminobutan-1-ol can also be prepared as follows:

5 of 2-nicotinoyl-1-methylvinylamine

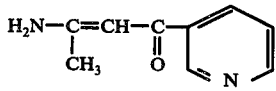

are dissolved in 50 ml of ethanol and a total of 6 g of sodium borohydride is added in portions over the course of 6 hours, at 70° C and with stirring. The mixture is then kept at 70° C for a further 10 hours. It is then concentrated, the residue is taken up in chloroform/water and the chloroform phase is separated off, dried and concentrated in vacuo (10 to 14 mm Hg). The residual oil is distilled. The fraction passing over between 125° and 150° C at 0.3 mm Hg is then dissolved in dioxane and the solution is treated with a solution of tartaric acid in dioxane. The slightly hygroscopic tartrate which is precipitated is filtered off, recrystallised from dimethylformamide/ethyl acetate and finally converted into the free base. This gives 1-(β-pyridyl)-3-aminobutan-1-ol in a 73% yield.

The 2-nicotinoyl-1-methylvinylamine required for the reduction can be prepared as follows:

7.5 g of nicotinoyl-acetone are dissolved in 45 ml of anhydrous ethanol and, after adding 20 ml of ammonia, the mixture is then stirred for 3 days at 50° C in an autoclave. Concentrating the clear solution leaves an oil which becomes solid after a short time. After recrystallisation from toluene, 2-nicotinoyl-1-methylvinylamine (melting point 82°) is obtained in a 91% yield.

EXAMPLE 4

2.6 g of 1-amino-3-(p-ethoxymethylenephenoxy)-propan-2-ol hydrochloride

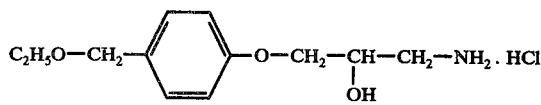

are suspended in 40 ml of ethanol, 1.8 g of the sodium salt of thenoyl-(2)-vinyl alcohol

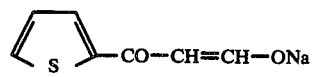

are then added and the mixture is stirred at room temperature for 24 hours. It is then filtered and the residue is washed with alcohol. The filtrate, including the alcohol washings, is concentrated in vacuo. An oil remains, which becomes solid after standing for a fairly long time and is recrystallised from dilute alcohol. This gives 1-(thenoyl-(2)-vinylamino)-3-(p-ethoxymethylenephenoxy)-propan-2-ol of the formula

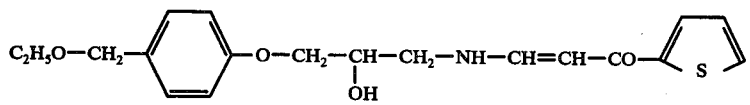

Melting point: 103° C
Analysis: (C$_{19}$H$_{23}$NO$_4$S)
calculated: C63.1 H 6.4 N 3.9
found: 62.9 6.5 3.9
Yield: 91% of theory.

The sodium salt of thenoyl-(2)-vinyl alcohol which is required can be prepared as follows:

32 g of 2-acetylthiophene and 18 g of ethyl formate are added dropwise over the course of 20 minutes, with stirring, to a suspension of 1.3 g of sodium methylate in 100 ml of absolute ether at a temperature of 10° to 15° C. The mixture is then allowed to stand at room temperature for 29 hours. It is then filtered and the residue is washed with a little absolute alcohol and then with ether. This gives the sodium salt of thenoyl-(2)-vinyl alcohol in a 95% yield.

EXAMPLE 5

2.5 g of 1-(p-methoxymethylenephenoxy)-3-amino-propan-2-ol hydrochloride

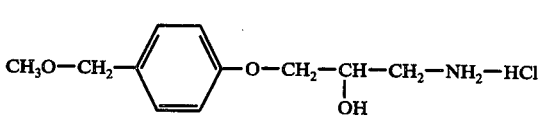

are suspended in 40 ml of ethanol, 1.6 g of the sodium salt of furoyl-(2)-vinyl alcohol

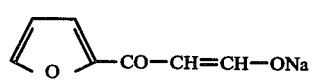

are then added and the mixture is stirred at room temperature for 24 hours. The mixture is then worked up as described in Example 4. This gives 1-(furoyl-(2)-vinylamino)-3-(p-methoxymethylenephenoxy)-propan-2-ol of the formula

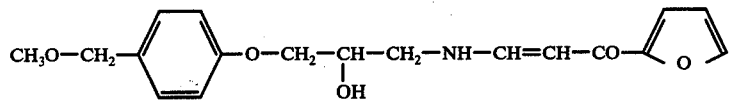

Melting point: 108° C
Analysis: (C$_{18}$N$_{21}$NO$_5$)
calculated: C 65.2 H 6.4 N 4.2
found: 65.4 6.5 4.0
Yield: 73% of theory.

The sodium salt of furoyl-(2)-vinyl alcohol which is required as the starting product can be prepared from 2-acetylfurane, ethyl acetate and sodium methylate, analogeously to the instructions for preparing the sodium salt of thenoyl-(2)-vinyl alcohol, as described in Example 4.

EXAMPLE 6

54.0 g of 1-(p-[4-methoxybutoxy]-phenoxy)-3-aminopropan-2-ol

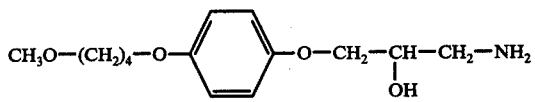

37.3 g of 6-methylnicotinoyl-acetone

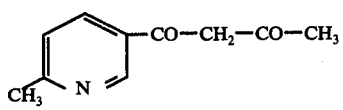

400 ml of ethanol and 0.1 ml of formic acid are heated to 50° for 1 hour and stirred at room temperature for a further 20 hours. Filtration gives 61.3 g of 1-(2-[6 -methylnicotinoyl]-1-methylvinylamino)-3-(p-[4-methoxybutoxy]-phenoxy)-propan-2-ol

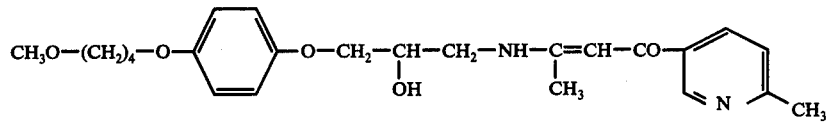

Melting points: 143°–145°. A further 15.0 g of the same substance can be obtained from the filtrate. Yield: 89% of theory.

19.0 g of this substance are dissolved at 70° in 200 ml of anhydrous ethanol. 6.0 g of sodium boranate are introduced in portions and the reaction mixture is heated at 70° for a further 7 hours and evaporated under reduced pressure. The residue is taken up in water and ethylene chloride and the clear ethylene chloride solution is thoroughly stirred with water and sufficient dilute sulphuric acid to make the pH value of the aqueous solution 6.5, and finally the latter is adjusted to pH 8. The base which is precipitated in this way as an oil is once more taken up in ethylene chloride and isolated in the usual manner. This gives 10.3 g of 1-[4-methoxybutoxy]-phenoxy)-3-(1-[2-methylpyridyl-5]-1-hydroxybutyl- 3-amino)-propan-2-ol

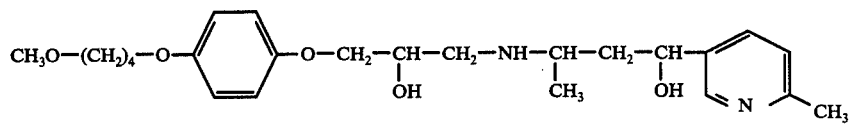

as a viscous oil; the neutral naphthalene-1,5 -disulphonate (containing 1/2 mol of the disulphonic acid) forms white, hygroscopic crystals, melting point 145°–150° (decomposition).
Analysis: (C$_{24}$H$_{36}$N$_2$O$_5$)
calculated: C 66.6 H 8.4 N 6.5 O 18.5
found: 66.4 8.4 6.3 18.8

The compounds listed in the following table were prepared in a manner corresponding to Examples 1–6.

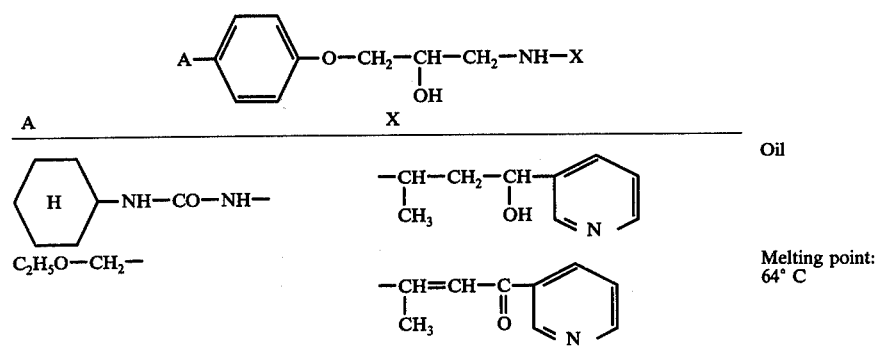

-continued $$A-\underset{}{\underset{}{\bigcirc}}-O-CH_2-\underset{OH}{CH}-CH_2-NH-X$$

| A | X | |
|---|---|---|
| $C_2H_5O-CH_2-$ | $-\underset{CH_3}{CH}-CH_2-\underset{OH}{CH}-\underset{}{\text{(3-pyridyl)}}$ | Oil |
| $C_2H_5-NH-CO-NH-$ | $-\underset{CH_3}{C}=CH-CO-\underset{}{\text{(3-pyridyl)}}$ | Melting point: 143° C |
| $C_2H_5-NH-CO-NH-$ | $-\underset{CH_3}{CH}-CH_2-\underset{OH}{CH}-\underset{}{\text{(3-pyridyl)}}$ | Melting point: 50° C (decomposition) |
| $C_2H_5O-CH_2-$ | $-CH_2-CH_2-\underset{OH}{CH}-\underset{}{\text{(2-thienyl)}}$ | Oil |
| $CH_3O-CH_2-$ | $-CH_2-CH_2-\underset{OH}{CH}-\underset{}{\text{(2-furyl)}}$ | Oil |
| $CH_3O-(CH_2)_4-O-$ | $-\underset{CH_3}{C}=CH-CO-\underset{}{\text{(4-(2-methylpyrimidinyl with CH_3))}}$ | Melting point: 79-81° C |
| $CH_3O-(CH_2)_4-O-$ | $-\underset{CH_3}{CH}-CH_2-\underset{OH}{CH}-\underset{}{\text{(pyrimidinyl)}}$ | Oil |
| cyclohexyl-$NH-CO-NH-$ | $-\underset{CH_3}{C}=CH-CO-\underset{}{\text{(pyrimidinyl)}}$ | Melting point: 179-180° C |
| cyclohexyl-$NH-CO-NH-$ | $-\underset{CH_3}{CH}-CH_2-\underset{OH}{CH}-\underset{}{\text{(pyrimidinyl)}}$ | Oil; salt containing ½ mol L-(+)-tartaric acid: melting point: 113-118 (decomposition) |
| $C_2H_5O-CH_2-$ | $-\underset{CH_3}{C}=CH-CO-\underset{}{\text{(6-methyl-3-pyridyl)}}$ | Melting point: 133-134° |
| $C_2H_5O-CH_2-$ | $-\underset{CH_3}{CH}-CH_2-\underset{OH}{CH}-\underset{}{\text{(6-methyl-3-pyridyl)}}$ | Oil |
| $C_2H_5-NH-CO-NH-$ | $-\underset{CH_3}{C}=CH-CO-\underset{}{\text{(2-methylpyrimidinyl)}}$ | Melting point: 155-157° |
| $C_2H_5-NH-CO-NH-$ | $-\underset{CH_3}{CH}-CH_2-\underset{OH}{CH}-\underset{}{\text{(pyrimidinyl)}}$ | Oil |
| $C_2H_5O-CH_2-$ | $-\underset{CH_3}{C}=CH-CO-\underset{}{\text{(pyrimidinyl)}}$ | Melting point: 105-106° |
| $C_2H_5O-CH_2-$ | $-\underset{CH_3}{CH}-CH_2-\underset{OH}{CH}-\underset{}{\text{(pyrimidinyl)}}$ | Oil; salt with ½ mol L-(+)-tartaric acid: melting point: 69-70°, hygroscopic |

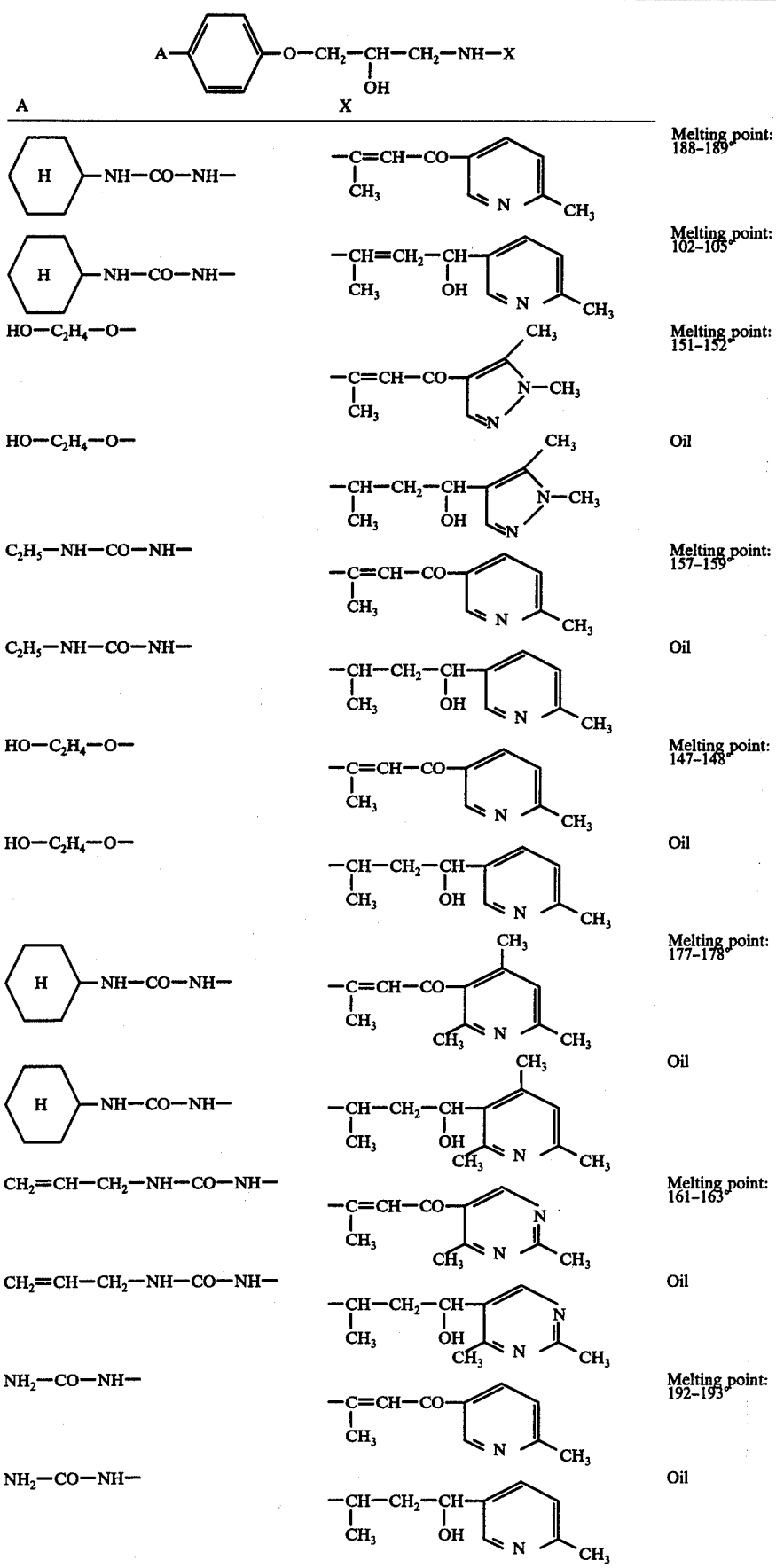

-continued $$A-\underset{}{\underset{|}{\underset{OH}{C_6H_4}}}-O-CH_2-CH-CH_2-NH-X$$

| A | X | |
|---|---|---|
| CH₃O—CH₂— | —C(CH₃)=CH—CO—O—(6-methylpyridin-3-yl) | Melting point: 118–119° |
| CH₃O—CH₂— | —CH(CH₃)—CH₂—CH(OH)—(6-methylpyridin-3-yl) | Oil |
| n-C₄H₉O—CH₂— | —C(CH₃)=CH—CO—O—(6-methylpyridin-3-yl) | Melting point: 107–108° |
| n-C₄H₉O—CH₂— | —CH(CH₃)—CH₂—CH(OH)—(6-methylpyridin-3-yl) | Oil |
| i-C₃H₇—NH—CO—NH— | —C(CH₃)=CH—CO—O—(2,4-dimethylpyrimidin-5-yl) | Melting point: 165–167° |
| i-C₃H₇—NH—CO—NH— | —CH(CH₃)—CH₂—CH(OH)—(2,4-dimethylpyrimidin-5-yl) | Oil |
| morpholine-N—CO—NH— | —C(CH₃)=CH—CO—O—(6-methylpyridin-3-yl) | Melting point: 185–188° |
| morpholine-N—CO—NH— | —CH(CH₃)—CH₂—CH(OH)—(6-methylpyridin-3-yl) | Oil |
| CH₃O—(CH₂)₄—O— | —CH=CH—CO—O—(2,4-dimethylpyrimidin-5-yl) | Melting point: 105–106° |
| CH₃O—(CH₂)₄—O— | —CH₂—CH₂—CH(OH)—(2,4-dimethylpyrimidin-5-yl) | Melting point: 109–110° |
| CH₃O—CH₂— | —CH(CH₃)—CH₂—CH(OH)—(pyridazin-3-yl) | Oil |
| C₂H₅O—C₂H₄—O— | —C(CH₃)=CH—CO—O—(6-methylpyridin-3-yl) | Melting point: 124–125° |
| C₂H₅O—C₂H₄—O— | —CH(CH₃)—CH₂—CH(OH)—(6-methylpyridin-3-yl) | Oil |
| C₂H₅O—C₂H₄—O— | —CH(CH₃)—CH₂—CH(OH)—(pyridin-3-yl) | Oil |
| CH₃O—CH₂ | —CH(CH₃)—CH₂—CH(OH)—(pyrazin-2-yl) | Oil |

-continued

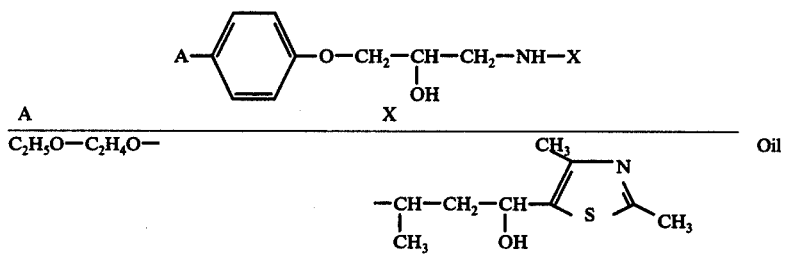

| A | X | |
|---|---|---|
| C₂H₅O—C₂H₄O— | 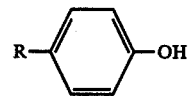 —CH—CH₂—CH— \| \| CH₃ OH | Oil |

Preparation of the starting diketones

The 6-methylnicotinoyl-acetone which is mentioned as the starting substance in Example 6, can be obtained in a known manner from α-picoline-5-carboxylic acid ethyl ester and acetone, or from 5-acetyl-α-picoline (prepared in accordance with Angew. Ch. 67, page 398) and ethyl acetate: 270 g of 5-acetyl-α-picoline, 5 l of anhydrous toluene, 387 g. of ethyl acetate and 537 g of potassium tert.-butylate are stirred at 40° for 20 hours and the mixture is subsequently decomposed by means of a mixture of 3 l of ice water and 288 ml of acetic acid. 283.5 g of 6-methylnicotinoyl-acetone, boiling point 108°-117°/0.2 mm Hg, which rapidly crystallises and, after recrystallisation from ligroin, melts at 57°-58°, is obtained in the usual manner from the toluene solution.

The following, inter alia, are obtained in a corresponding manner:
- 2,4-dimethyl-5-pyrimidylcarbonyl-acetone Melting point: 65°-66°
- 2,4,6-trimethyl-nicotinoyl-acetone Oil, boiling point 98°-107°/0.2 mm Hg
- 1,5-dimethyl-4-pyrazolylcarbonyl-acetone Oil, boiling point 108°-110°/0.1 mm Hg.
- 4-methyl-5-pyrimidylcarbonyl-acetone Melting point: 52°-54°
- 2-methyl-4-ethyl-5-pyrimidylcarbonyl-acetone Melting point: 35°-37°
- 2-thenoyl-acetone Melting point: 32°-33°
- 2,4-dimethyl-5-thiazolylcarbonyl-acetone Oil, boiling point 93°-98° /0.15 mm Hg
- 2,5-dimethyl-3-theonyl-acetone Oil, boiling point 104°-111°/0.1 mm Hg
- 3-pyridazinylcarbonyl-acetone Melting point: 110°-112°

Preparation of the starting amines

The following substances are obtained by reacting the phenols

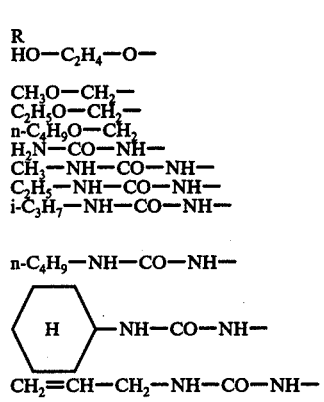

with epichlorohydrin and then with ammonia in the manner described in Example 1 (if R contains a urea group >N-Co NH—, the distillation is replaced by recrystallisation):

| R | 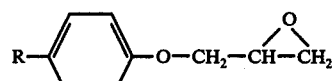 | 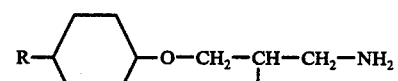 |
|---|---|---|
| HO—C₂H₄—O— | Melting point: 48-52° (crude) | Melting point: 104-106° |
| CH₃O—CH₂— | Oil, boiling point 105-106°/0.1 mm Hg | Melting point: 59-60° |
| C₂H₅O—CH₂— | Oil, boiling point 120-124°/0.1 mm Hg | Melting point: 54-56° |
| n-C₄H₉O—CH₂ | Oil, boiling point 124-130°/0.1 mm Hg | Melting point: 66-68° |
| H₂N—CO—NH— | Melting point: 149-150° | Melting point: 141-143° |
| CH₃—NH—CO—NH— | Melting point: 146-147° | Melting point: 151-153° |
| C₂H₅—NH—CO—NH— | Melting point: 148-150° | Melting point: 140-141° |
| i-C₃H₇—NH—CO—NH— | Melting point: 176-177° | Melting point: 150-151°, solid again at 161° and melts again at 216-218° |
| n-C₄H₉—NH—CO—NH— | Melting point: 143-144° | Melting point: 134-136° |
| ⟨H⟩—NH—CO—NH— | Melting point: 179-180° | Melting point: 162-163° |
| CH₂=CH—CH₂—NH—CO—NH— | Melting point: 143-144° | Melting point: 145-147° |

The 4-alkoxymethylphenols used as the starting substances are readily accessible from 4-hydroxymethylphenol in accordance with Rec. 74, page 1448.

The N-substituted ureidophenols used as the starting substances can be obtained, either from p-aminophenol using (cyclo-) alkylisocyanates or from N-(p-hydroxyphenyl)-0-phenylurethane using primary or secondary amines:

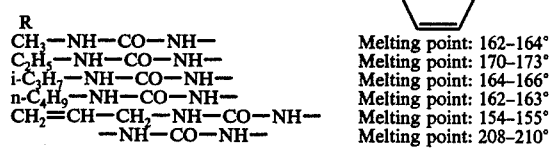

| R | |
|---|---|
| CH₃—NH—CO—NH— | Melting point: 162-164° |
| C₂H₅—NH—CO—NH— | Melting point: 170-173° |
| i-C₃H₇—NH—CO—NH— | Melting point: 164-166° |
| n-C₄H₉—NH—CO—NH— | Melting point: 162-163° |
| CH₂=CH—CH₂—NH—CO—NH— | Melting point: 154-155° |
| —NH—CO—NH— | Melting point: 208-210° |

-continued

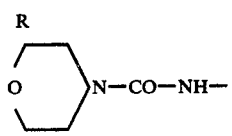 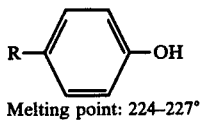

Melting point: 224–227°

EXAMPLE 7

2.0 g of 1-(p-[4-methoxybutoxy]-phenoxy)-3-(1- [2-methylpyridyl-5]-1-hydroxybutyl-3-amino)-propan-2-ol (compare Example 6) of the formula

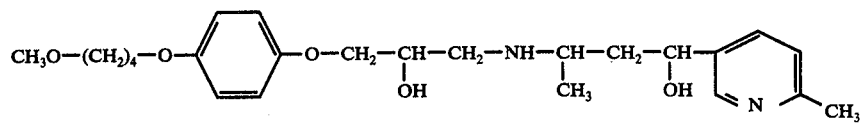

are heated under reflux together with 20 ml of ethanol and 0.50 ml of a 39 % strength aqueous formaldehyde solution, for 4 hours. The reaction mixture is evaporated and the residue is taken up in 200 ml of ligroin. Evaporation of the solution, after clarification by means of a little active charcoal, gives 1.8 g of 3-(1-hydroxy-1-[2-methylpyridyl-5]-3-butyl)-5-(4-[4-methoxybutoxy]-phenoxymethyl)-oxazolidine of the formula

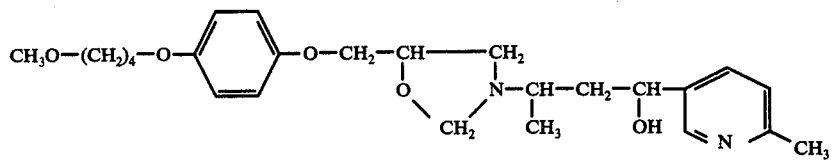

as a colourless oil.
Analysis: ($C_{25}H_{36}N_2O_5$)
calculated: C 67.5 H 8.2 N 6.3 O 18.0 found: 67.3 8.2 6.2 18.2

What we claim is:

1. A compound of the formula

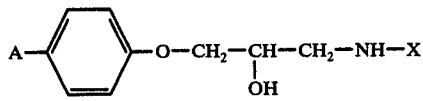

wherein X

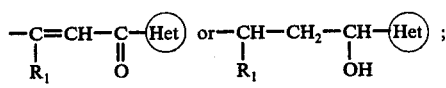

A is —$CH_2$-alkoxy, -O-alkoxyalkyl, -O-hydroxyalkyl or

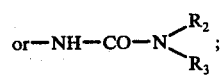

$R_1$ is -H or methyl;

(Het) is pyrimidinyl which is optionally substituted by up to three methyl groups; and
each of
$R_2$ and $R_3$ is, independently, -H, alkyl, alkenyl or cycloalkyl; each alkyl having from 1 tp 4 carbon atoms, each alkoxy having from 1 to 4 carbon atoms, each alkenyl having 3 or 4 carbon atoms and each cycloalkyl having from 5 to 7 carbon atoms;
or a pharmaceutically-acceptable acid-addition salt thereof.

2. A compound according to claim 1 wherein X is

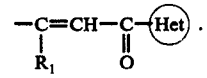

3. A compound according to claim 1 wherein X is

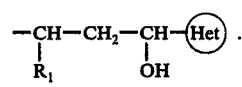

4. A compound according to claim 1 wherein the pyrimidinyl is 2,4-dimethyl-pyrimidinyl-5.

5. 1-(p-Allylureido-phenoxy)-3-[1-(2,4- dimethyl-pyrimidinyl-5)-1-hydroxybutyl-3-amino]propan-2-ol or a pharmaceutically-acceptable acid-addition salt thereof.

6. 1-(p-Methoxybutoxy-phenoxy)-3-[1-(2,4-dimethyl-pyrimidinyl-5)-1-hydroxybutyl-3-amino]propane-2-ol or a pharmaceutically-acceptabel acid-addition salt thereof.

7. 1-(p-Ethylureido-phenoxy)-3-[1-(2,4-dimethyl-pyrimidinyl-5)-1-hydroxybutyl-3-amino]propan-2-ol or a pharmaceutically-acceptable acid-addition salt thereof.

8. 1-(p-Isopropylureido-phenoxy)-3-[1-(2,4-dimethyl-pyrimidinyl-5)-1-hydroxybutyl-3-amino]propan-2-ol or a pharmaceutically-acceptable acid-addition salt thereof.

9. 1-(p-Cyclohexylureido-phenoxy)-3-[1- (2,4-dimethylpyrimidinyl-5)-1-hydroxybutyl-3-amino]propan-2-ol or a pharmaceutically-acceptable acid-addition salt thereof.

10. 1-(p-Ethoxymethylene-phenoxy)-3-[1(2,4-dimethylpyrimidinyl-5)-1-hydroxybutyl-3-amino]propan-2-ol or a pharmaceutically-acceptable acid-addition salt thereof.

11. A pharmaceutically-acceptable β-adrenergic-blocking composition comprising diluent or excipient and an effective concentration of a compound according to claim 1.

12. A pharmaceutically-acceptable composition comprising diluent or excipient and a β-adrenergic-blocking-effective concentration of a comound according to claim 3.

13. A pharmaceutically-acceptable β-adrenergic-blocking composition comprising diluent or excipient and an effective concentration of a compound according to claim 5.

* * * * *